(12) United States Patent
Fares et al.

(10) Patent No.: US 9,423,326 B1
(45) Date of Patent: Aug. 23, 2016

(54) METHOD OF OBTAINING SIMULATED PORE WATER

(71) Applicants: Galal Fares, Riyadh (SA); Mohammad Iqbal Khan, Riyadh (SA)

(72) Inventors: Galal Fares, Riyadh (SA); Mohammad Iqbal Khan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 14/922,106

(22) Filed: Oct. 23, 2015

(51) Int. Cl.
*G01N 1/38* (2006.01)
*G01N 1/40* (2006.01)
*G01N 33/38* (2006.01)

(52) U.S. Cl.
CPC ............... *G01N 1/4022* (2013.01); *G01N 1/38* (2013.01); *G01N 33/383* (2013.01); *G01N 2001/4027* (2013.01)

(58) Field of Classification Search
None
See application file for complete search history.

(56) References Cited

U.S. PATENT DOCUMENTS

| | | | | |
|---|---|---|---|---|
| 4,196,614 A * | 4/1980 | McLaughlin | ........ | G01N 33/383 73/54.03 |
| 5,002,399 A * | 3/1991 | Akinc | ................ | G01N 15/0893 374/14 |
| 5,396,790 A * | 3/1995 | Koelliker | ............. | G01N 33/383 73/54.03 |
| 7,117,946 B2 * | 10/2006 | Herr | ........................ | E21B 43/16 166/369 |
| 7,401,501 B2 * | 7/2008 | Lockwood | ......... | G01N 21/4738 366/139 |
| 7,753,120 B2 * | 7/2010 | Keller | ..................... | E21B 43/08 166/207 |
| 2008/0264872 A1 * | 10/2008 | Konishi | ............... | B01D 9/0022 210/710 |

\* cited by examiner

*Primary Examiner* — Hezron E Williams
*Assistant Examiner* — Mark A Shabman
(74) *Attorney, Agent, or Firm* — Richard C. Litman

(57) ABSTRACT

The method of obtaining simulated pore water includes: mixing cement with a quantity of water and waiting a period of time for water-soluble salts in the cement to dissolve; filtering the mixture; evaporating an aliquot of the filtrate; weighing solids obtained by evaporating the aliquot to determine total dissolved solids or salts in the aliquot; weighing the remaining filtrate and measuring its volume; determining the mass of total dissolved solids in the remaining filtrate; determining the mass of water in remaining filtrate; determining the mass of water that would be in the remaining filtrate if the mix had been prepared with a desired W/C ratio; evaporating any difference between the mass of the remaining filtrate and the mass that would be present at the desired W/C; and collecting the filtrate remaining as simulated pore water for the desired W/C ratio which may be used for a variety of different applications.

5 Claims, 2 Drawing Sheets

METHOD OF OBTAINING SIMULATED PORE WATER

BACKGROUND OF THE INVENTION

1. Field of the Invention

The present invention relates to the measurement and testing of cement, and particularly to a method of obtaining simulated pore water from cement in sufficient quantities for extraction and analysis thereof.

2. Description of the Related Art

Concrete is prepared from a mixture of cement, water, and an aggregate (sand, stone, gravel, etc.), which is generally assumed to be inert. When first mixed, the materials form a plastic-like mass that can be formed into the desired shape by a mold or the like. As the material cures, a chemical reaction called hydration takes place between the cement and the water, causing the concrete to harden into a stone-like condition in which the hydrated cement holds the aggregate in place. The properties of the resulting concrete are affected by the water-to-cement (W/C) ratio, the composition of the cement, and other factors. Sometimes an admixture or additive is added to the mix to accelerate or retard the initial set of the concrete, to improve workability, to reduce water requirements, to increase strength, or to otherwise alter the properties of the concrete. Admixtures may include accelerators, retardants, air-entraining agents, workability agents, dampproofing and permeability reducing agents, pozzolans, color pigments, and other additives.

Although the vast majority of the water is consumed by hydration or evaporation as the mix hardens or cures, concrete is porous, and a small amount of the water, referred to as "pore water", may be entrapped in pores or channels in the concrete. It is believed that the pore water may produce undesirable effects affecting the properties of the concrete. Thus, the pore water may cause leaching of salts, corrosion of steel reinforcement embedded in the concrete, or other effects diminishing the strength, durability, permeability, or other properties of the concrete. The water in the initial mix or cement paste is also referred to as pore water, being the precursor of pore water found in the hardened concrete.

Therefore, part of the testing of concrete involves the analysis of pore water for pH, salt content, etc. Conventional methods for obtaining pore water include high-speed centrifuging of the cement paste when it is in the plastic state, or crushing the paste and using a press if the paste has hardened too much for centrifuging. However, the quantity of pore water obtained by such methods is always small, and particularly when the water-to-cement ratio is low, the quantity of pore water obtained may be too small to perform the desired analysis.

Thus, a method of obtaining simulated pore water solving the aforementioned problems is desired.

SUMMARY OF THE INVENTION

The method of obtaining simulated pore water is a method of producing simulated pore water from a cement paste in quantities sufficient for analysis and study. The method includes the following steps: mixing cement with an excess quantity of water and waiting a sufficient period of time for the salts in the cement to dissolve; filtering the mixture and discarding any solids obtained; evaporating an aliquot of the filtrate; weighing any solids obtained by evaporating the aliquot to determine the total dissolved solids or total dissolved salts (TDS) in the aliquot; weighing the remaining filtrate ($M_f$) and measure its volume ($V_f$); determining the mass of total dissolved solids ($M_{TDS}$) in the remaining filtrate; determining the mass of water ($M_w$) in remaining filtrate ($M_w=M_f-M_{TDS}$); determining the mass of water that would be in the remaining filtrate ($M_{W/C}$) if the mix had been prepared with a desired W/C ratio; evaporating any difference between the mass of the remaining filtrate and the mass that would be present at the desired W/C (amount to be evaporated=Mw–$M_{W/C}$); collecting the filtrate remaining after the preceding evaporating step as simulated pore water for the desired W/C ratio.

The method assumes that when cement is added to a sufficient excess amount of water and stirred for a sufficient amount of time, all soluble salts will dissolve in the water and be in the filtrate following filtration. It is noted that the simulated pore water is representative of "initial" pore water (i.e., pore water at the initial stage of cement contact with water), as opposed to gel or capillary water.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
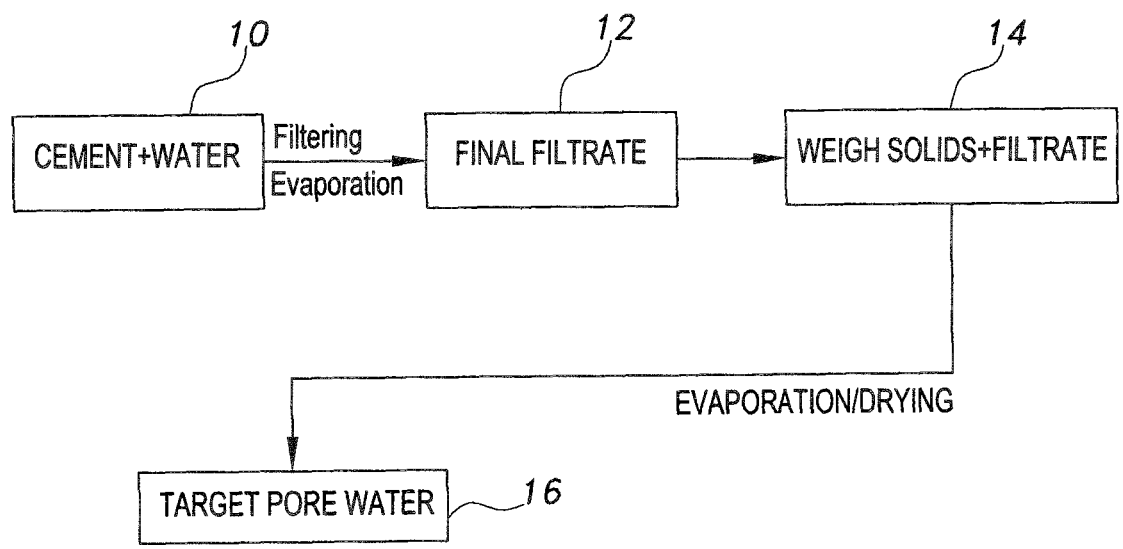
FIG. 1 is a block diagram representing an overview of the method of obtaining simulated pore water according to the present invention.

The method of obtaining simulated pore water is a method of producing simulated pore water from a cement paste in quantities sufficient for analysis and study. The method includes the following steps: mixing cement with an excess quantity of water and waiting a sufficient period of time for the salts in the cement to dissolve; filtering the mixture and discarding any solids obtained; evaporating an aliquot of the filtrate; weighing any solids obtained by evaporating the aliquot to determine the total dissolved solids or total dissolved salts (TDS) in the aliquot; weighing the remaining filtrate ($M_f$) and measure its volume ($V_f$); determining the mass of total dissolved solids ($M_{TDS}$) in the remaining filtrate; determining the mass of water ($M_w$) in remaining filtrate ($M_w=M_f-M_{TDS}$); determining the mass of water that would be in the remaining filtrate ($M_{W/C}$) if the mix had been prepared with a desired W/C ratio; evaporating any difference between the mass of the remaining filtrate and the mass that would be present at the desired W/C (amount to be evaporated=Mw–$M_{W/C}$); collecting the filtrate remaining after the preceding evaporating step as simulated pore water for the desired W/C ratio.

An initial mass of cement, $m_{c0}$, is first added to an initial volume of water, $v_{c0}$, to form an initial cement mix, such that water-soluble salts of the initial mass of cement are fully dissolved in the initial volume of water; i.e., the dissolved salts are in solution. This is represented as step 10 in FIG. 1 and as step 20 in FIG. 2, where a desired W/C is shown as being preferably greater than or equal to 2, although it should be understood that any other desired proportions may be used with cement.

For a typical exemplary mass of cement of 50 g and a typical exemplary mass of water of 100 mL, the time sufficient for complete free dissolution of the salts in the water is typically about 30 minutes. This example, with a water-to-cement ratio of 2:1 by weight (assuming that the density of water is 1 g/mL), shows that cement mixed with an excess of water (compared against typical cement) is preferred. It should be understood that this water-to-cement ratio is given for exemplary purposes only. A greater quantity of water may be used, provided that the quantity of water is sufficiently in excess of the mass of cement to ensure that all water-soluble salts are in solution. Further, the method may also be used on cement containing an admixture of additives (e.g., accelerators, retardants, etc.), in which case the mass of the additives is included in the mass of cement when determining the amount of water that may be required.

The initial cement mix is then filtered to produce a filtrate. It should be understood that any suitable type of filtering may be utilized, such as gravity filtration, vacuum filtration, etc., so long as no remaining fine particulate matter remains in the filtrate. The filtrate contains all of the dissolved salts from the cement mix. The filtrate is weighed to determine the mass of the filtrate, $m_f$. Any solids obtained by filtration are discarded.

Figure 2:
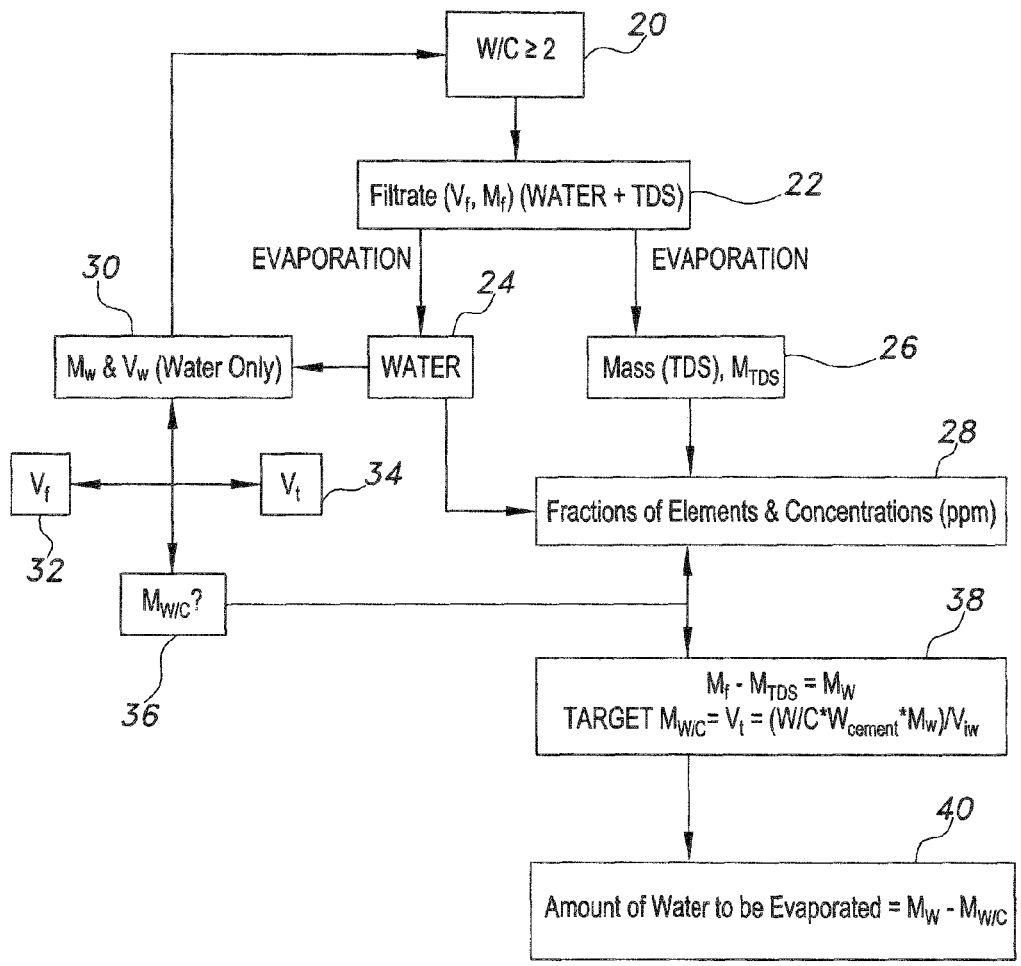
FIG. 2 is a flow chart of the method of obtaining simulated pore water according to the present invention.

At step 12 and step 22 of FIGS. 1 and 2, respectively, an aliquot or portion of the filtrate is evaporated using any suitable technique for evaporation. For example, if 70 mL of filtrate is obtained by filtering the mixture, then a 10 mL aliquot of the filtrate might be evaporated. The solids obtained by evaporation of the aliquot may be dried. Drying may be performed by conventional oven drying or the like. The dried solids are then weighed to determine the mass of the solids in the aliquot (step 14). For example, if the dried solids weigh 0.0025 g (2500 µg), and if the density of water is 1 g/mL, then the filtrate contains total dissolved solids determined by:

$$\frac{0.0025 \text{ g} \times 1000 \text{ mg/g}}{(10^{-3} \text{ L/mL} \times 10 \text{ mL})} = 250 \frac{\text{mg}}{\text{L}} = 250 \text{ ppm}.$$

The volume of the filtrate ($V_f$) after removal of the aliquot is 60 mL. The mass of the filtrate ($M_f$) after removal of the aliquot is determined by weighing the remaining filtrate. The mass of the total dissolved solids ($M_{TDS}$) in the remaining filtrate may be calculated as follows (step 26):

$$\frac{M_{TDS}}{V_f} = \frac{\text{mass of solids in aliquot}}{\text{volume of aliquot}},$$

or using the numbers in the above example:

$$M_{TDS} = \frac{0.0025 \text{ g}}{10 \text{ mL}} \times 60 \text{ mL} = 0.125 \text{ g}.$$

The mass of the water ($M_w$) in the filtrate remaining after removal of the aliquot may then be calculated as $M_w = M_f - M_{TDS}$ (steps 24, 30, 32, 36). The mass of the water that would be in the filtrate remaining after removal of the aliquot for a desired W/C ratio may then be determined as follows. The mass of the mix water for the desired W/C ratio is the mass of the cement multiplied by the W/C ratio. The method assumes that the volume of filtrate obtained after filtering the mix prepared at the desired W/C ratio is proportional to the volume of filtrate obtained after filtering the mix prepared with an excess of water (e.g., a W/C ration of 2:1). Therefore, the mass of the mix water for the desired W/C ratio is multiplied by the ratio of the volume of filtrate obtained after filtration when prepared with excess water to the volume of mix water when prepared with an excess of water to obtain the volume of filtrate that would be obtained from a mix prepared at the desired W/C ratio. Mathematically, this may be expressed by:

$$M_{W/C} = (W/C * W_{cement} * V_{filtrate})/V_{iw},$$

where $M_{W/C}$ is the mass of water in the filtrate when prepared at the desired W/C ratio, W/C is the desired W/C ratio, $W_{cement}$ is the mass of cement in the mix, $V_{filtrate}$ is the volume of filtrate obtained after filtering a mix prepared with excess water, and $V_{iw}$ is the volume of water used to prepare the mix with excess water (steps 28, 38). If the volumes are converted to mass by multiplication by the density of water, this equation may be expressed as:

$$M_{W/C} = (W/C * W_{cement} * M_{wf})/M_{iw},$$

where $M_{wf}$ is the mass of the water in the filtrate (without total dissolved solids) obtained from a mix prepared with excess water and $M_{iw}$ is the weight of the mix water when prepared with excess water. The mass of the water remaining in the filtrate after removal of the aliquot is the calculated by subtracting the mass of the aliquot from $M_{W/C}$. The amount of water to be evaporated from the filtrate remaining after removal of the aliquot to obtain the simulated pore water is given by subtracting this last quantity from $M_w$ (step 40). The obtained pore water (indicated as 16 in FIG. 1) may be used for a variety of applications, such as evaluating the effect of pore water composition on any desired property; e.g., hydration, corrosion, superpolymer absorption-desorption mechanisms, etc.

It should be noted that this project was funded by the National Plan for Science, Technology and Innovation (MAARIFAH), King Abdulaziz City for Science and Technology, Kingdom of Saudi Arabia, Award Number 12-ADV2591-02.

It is to be understood that the present invention is not limited to the embodiments described above, but encompasses any and all embodiments within the scope of the following claims.

We claim:

1. A method of obtaining simulated pore water for a predetermined water-to-cement (W/C) ratio, comprising the steps of:

mixing a first quantity of cement with a first quantity of water exceeding the predetermined W/C ratio;

allowing the salts in the cement to dissolve, resulting in a water-cement mixture;

filtering the mixture and discarding any solids obtained, retaining the filtrate;

evaporating an aliquot of the filtrate;

weighing any solids obtained by evaporating the aliquot to determine total dissolved solids (TDS) in the aliquot;

weighing the filtrate remaining after removal of the aliquot to obtain its mass and measuring its volume;

determining the mass of total dissolved solids (MTDS) in the remaining filtrate;

subtracting the mass of the total dissolved solids from the mass of the filtrate remaining after removal of the aliquot to determine the mass of water in the remaining filtrate;

determining the theoretical mass of water that would be in the remaining filtrate after removal of the aliquot if the mix had been prepared with the predetermined W/C ratio;

evaporating any difference between the mass of the remaining filtrate and the mass of filtrate that would be present at the predetermined W/C; and collecting the filtrate remaining after the preceding evaporating step as simulated pore water corresponding to the predetermined W/C ratio.

2. The method of obtaining simulated pore water according to claim 1, wherein said excess quantity of water comprises a W/C ratio of 2:1 by weight.

3. The method of obtaining simulated pore water according to claim 1, wherein the time for salts in the cement to dissolve comprises 30 minutes.

4. The method of obtaining simulated pore water according to claim 1, wherein said step of determining the mass of total dissolved solids (MTDS) in the remaining filtrate comprises the step of multiplying the volume of the remaining filtrate by the ratio of the solids obtained by evaporating the aliquot to the mass of the aliquot.

5. The method of obtaining simulated pore water according to claim 1, wherein said step of determining the theoretical mass of water that would be in the remaining filtrate after removal of the aliquot if the mix had been prepared with the predetermined W/C ratio comprises the steps of:

multiplying the mass of cement in the mix by the predetermined W/C ratio to obtain the theoretical mass of water with no dissolved solids at the predetermined W/C ratio;

multiplying the theoretical mass of water with no dissolved solids at the predetermined W/C ratio by the ratio of the mass of filtrate obtained by filtering the water-cement mixture prepared with the first quantity of water to the mass of the first quantity of water to obtain the expected mass of filtrate at the predetermined W/C ratio; and subtracting the mass of the aliquot from the expected mass of filtrate at the desired W/C ratio to obtain the mass of water that would be in the remaining filtrate after removal of the aliquot if the mix had been prepared with a desired W/C ratio.

* * * * *